United States Patent [19]

Takano et al.

[11] Patent Number: 4,898,177

[45] Date of Patent: Feb. 6, 1990

[54] ULTRASONIC PROBE WITH FINGER GRIP ADAPTER

[75] Inventors: Masayuki Takano; Susumu Hiki, both of Ootawara; Yuusiti Kikuti, Nasu, all of Japan

[73] Assignee: Kabushiki Kaisha Toshiba, Kawasaki, Japan

[21] Appl. No.: 172,546

[22] Filed: Mar. 24, 1988

[30] Foreign Application Priority Data

Mar. 26, 1987 [JP] Japan .................. 62-45426[U]

[51] Int. Cl.⁴ .............................................. A61B 8/00
[52] U.S. Cl. ............................................... 128/662.03
[58] Field of Search .................. 128/660.01, 660.1, 662.03–662.06; 73/633

[56] References Cited

U.S. PATENT DOCUMENTS

| 4,402,324 | 9/1983 | Lindgren et al. | 128/662.05 |
| 4,742,829 | 5/1988 | Law et al. | 128/662.05 |

FOREIGN PATENT DOCUMENTS 3810289 4/1989 Fed. Rep. of Germany .......... 128/662.03

OTHER PUBLICATIONS

"Use of Ultrasonic Reflectoscope for Continuous Recording of Movements of Heart Walls," I. Edler; C. H. Hertz, ECHOPAN-KS 1954.

Primary Examiner—Francis Jaworski
Attorney, Agent, or Firm—Cushman, Darby & Cushman

[57] ABSTRACT

A pencil type ultrasonic probe to which a finger grip adapter is attached is fixed to a cable connected to an ultrasonic diagnosis apparatus. Operator's fingers are hooked on the adapter attached to the probe to allow the probe to be held by an operator's hand, thereby keeping the probe at a predetermined position of an organic body. The adapter comprises: a body having a through-hole in which the probe is inserted; and a finger grip portion extending from the body and allowing the operator's fingers to be hooked on. The body has a guide slit for allowing the cable to pass therethrough. Thus, the cable is guided into the through-hole through the guide slit, and the probe is inserted into the through-hole to be attached to the adapter. When the probe is pulled out from the through-hole of the body, the cable is located in the through-hole. Thereafter, the cable is taken out from the through-hole through the guide slit, so that the adapter can be quickly and easily detached from the cable.

9 Claims, 5 Drawing Sheets

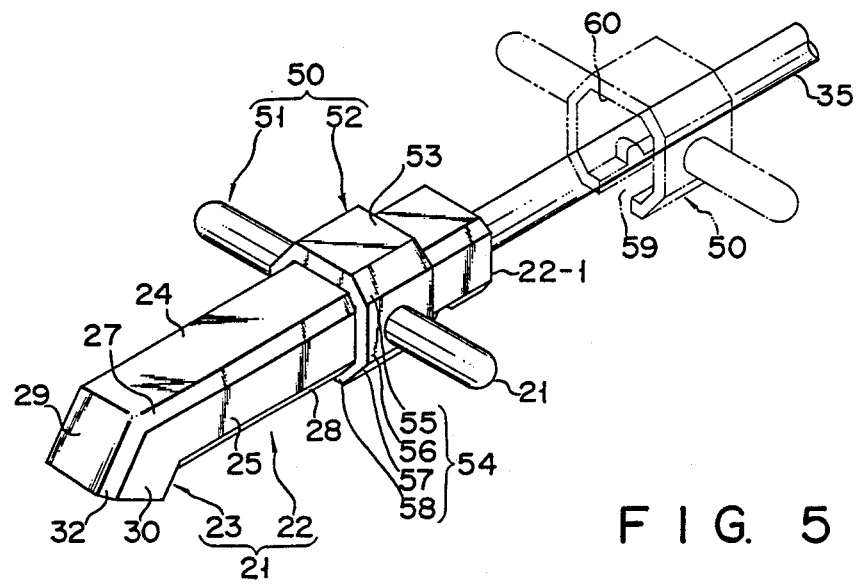
FIG. 5
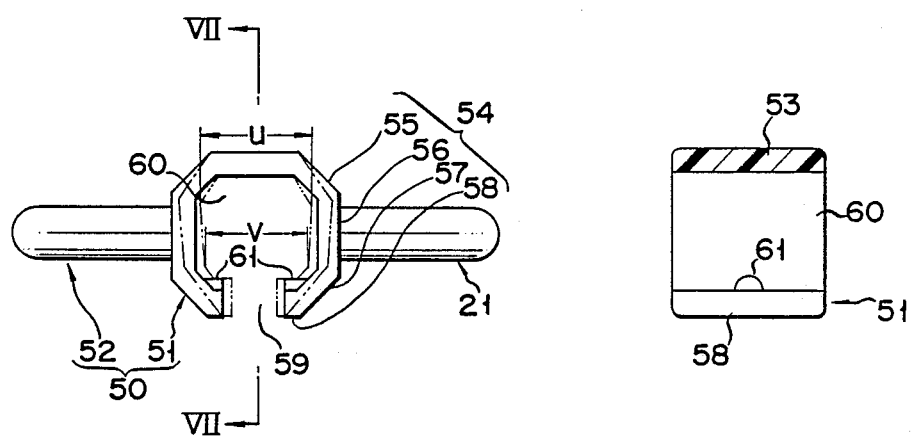
FIG. 6
FIG. 7

ULTRASONIC PROBE WITH FINGER GRIP ADAPTER

BACKGROUND OF THE INVENTION

1. Field of the Invention

The present invention relates to a pencil type ultrasonic probe provided with a finger grip adapter and, more particularly, to the ultrasonic probe provided with the adapter on which operator's fingers can be hooked to allow the ultrasonic probe to be held by the operator, so that a beam radiation surface of the ultrasonic probe can be stably held with respect to a body surface of a patient to be examined during an ultrasonic diagnosis.

2. Description of the Related Art

In an ultrasonic diagnosis, an ultrasonic probe is brought into contact with a body surface of a patient to be examined. An ultrasonic beam is emitted from a beam radiation surface of the ultrasonic probe onto the patient. The ultrasonic beam (echo) reflected inside the patient is detected by the ultrasonic probe through the beam radiation surface and converted into an electric signal. The electric signal is transmitted to an ultrasonic diagnosis apparatus and electrically processed therein. As a result, for example, a tomographic image inside the patient can be obtained, and a moving portion in the patient can be observed or the flow speed of the blood can be measured.

When a patient whose body size is relatively small, e.g., a child or newborn baby, is to be subjected to an ultrasonic diagnosis, a pencil type ultrasonic probe is sometimes used, which is smaller in size than a normal ultrasonic probe and has a relatively narrow range of performing an ultrasonic diagnosis. The pencil type ultrasonic probes can be categorized into two types, i.e., one having only one transducer element (single type) and the other having a plurality of transducer elements. In the former type, changes in a moving portion with a lapse of time can be observed using the M mode, and the flow speed of the blood can be measured using the Doppler mode. In the latter type, in addition to the above functions, a tomographic image inside the patient can be obtained using the B mode, while the probe is kept at the same position.

In order to accurately execute an ultrasonic diagnosis, the beam radiation surface of this pencil type ultrasonic probe must be stably held with respect to the patient's body surface. Especially, in the probe of the latter type, since a tomographic image is taken, the probe must held more stably than the probe of the former type. However, the pencil type ultrasonic probe is smaller in size than the normal probe. More specifically, this probe has a narrow and elongated shape. For this reason, it is very difficult for the operator to stably hold this probe with his hand. Sometimes, an adapter is attached to the pencil type ultrasonic probe. The operator's fingers can grasp this adapter so that the probe can be held by the operator's hand. As shown in FIG. 8, index and middle fingers are hooked on finger grip portion 52 protruding from adapter 50, and the probe is held between the index and middle fingers. When the adapter is attached to the probe, since a relatively large number of portions of the probe are supported by the fingers, the probe can be stably held.

As shown in FIG. 9, however, some operator may prefer to operate the probe without attaching the adapter to the probe. In addition, the adapter need be detached from the probe to allow the probe to be stored in a predetermined place. For this purpose, this adapter is designed to be detachably mounted on the probe.

FIGS. 1 and 2 show conventional adapters, respectively (note that a probe shown in FIGS. 1 and 2 is of a single type). Probe 1 shown in FIG. 1 comprises extended portion 2 extended by a predetermined length, to which cable 7 extending from an ultrasonic diagnosis apparatus (not shown) is attached, and distal end portion 3, which is bent at a predetermined angle with respect to extended portion 2 and stores a transducer element. Adapter 4 comprises body 5 formed into a ring-like shape corresponding to the outer shape of extended portion 3, and finger grip portion 6 protruding from body 5.

Adapter 4 shown in FIG. 1 can be attached/detached to/from probe 1. However, when adapter 4 is detached from extended portion of probe 1, since distal end portion 3 of probe 1 is bent with respect to extended portion 2, body 5 of adapter 4 cannot pass through distal end portion 3. For this reason, adapter 4 is moved toward cable 7. Since body 5 of adapter 4 has the ring-like shape, adapter 4 cannot be detached from cable 7. In such a case, if the operator operates the probe with detaching the adapter therefrom, the adapter may hit the operator's arm or hand. For this reason, during an ultrasonic diagnosis, the adapter may interfere with the operation of the probe.

Adapter 10 shown in FIG. 2 comprises body 11, in which a through-hole is formed to allow insertion of an extended portion of probe 1 and female thread portions are formed, and a pair of finger grip portions 12, each of which has a male thread portion formed at its distal end to be meshed with a corresponding one of the female thread portions and on each of which the operator's fingers can be hooked. When adapter 10 is to be attached to probe 1, the male thread portions of finger grip portions 12 are rotated in a direction allowing the male thread portions to be fastened to the female threads of body 11, and the distal ends of the male threads are brought into contact with extended portion 12 of probe 1. With this operation, adapter 10 is attached to probe 1 at a proper position of the extended portion. When adapter 10 is detached from probe 1, the male thread portions of finger grip portions 12 are rotated in a direction allowing the male thread portions to be loosened from the female thread portions of body 11, and the distal ends of the male thread portions are separated from extended portion 12 of probe 1. With this operation, the adapter is detached from the probe. In this case, finger grip portions 12 may be detached from the body.

Similar to the case in FIG. 1, however, when adapter 10 is detached from probe 1, since distal end portion 3 of probe 1 is bent with respect to extended portion 2, distal end portion 3 cannot pass through a through-hole of body 11 of adapter 10. For this reason, body 11 of adapter 10 is moved toward cable 7. Since cable 7 is inserted in the through-hole of body 11 of adapter 10, adapter 10 cannot be detached from cable 7. Thus, similar to the case in FIG. 1, when the operator operates the probe without attaching the adapter thereto, the adapter may interfere with the operator who is operating the probe.

In addition, the adapter shown in FIG. 2 has a large structure. Therefore, when the adapter is attached to the probe, the operator's fingers may not be stably hooked on the finger grip portions of the adapter.

Furthermore, since the adapter is attached/detached to/from the probe using the thread, the adapter cannot be detached from the probe quickly, and hence the operation for attachment/detachment of the adapter is cumbersome. Moreover, when the adapter is attached to the probe, if the thread is loosened, the adapter may be rotated around the extended portion of the probe. For this reason, the operator's fingers may not stably hold the finger grip portions of the adapter.

SUMMARY OF THE INVENTION

It is an object of the present invention to provide a pencil type ultrasonic probe provided with a finger grip adapter which can be completely detached from the probe and its cable, thereby improving operability in attachment/detachment.

It is another object of the present invention to provide a pencil type ultrasonic probe provided with a finger grip adapter which has a simple structure allowing the adapter to be stably attached to the probe and quickly and easily detached therefrom.

It is still another object of the present invention to provide a pencil type ultrasonic probe provided with a finger grip adapter which can be quickly and easily attached to an arbitrary position of the probe, thereby improving operability in attachment/detachment.

According to the present invention, there is provided a pencil type ultrasonic probe provided with a finger grip adapter, the ultrasonic probe being fixed to a cable which can be connected to an ultrasonic diagnosis apparatus, operator's fingers being adapted to be hooked on the adapter attached to the ultrasonic probe to allow the probe to be held by an operator's hand, thereby keeping the ultrasonic probe at a predetermined position of the organic body, the ultrasonic probe and the cable constituting a probe assembly, the adapter, comprising:
 a body including a through-hole in which the ultrasonic probe is inserted to cause the adapter to be attached to the ultrasonic probe, a guide slit for allowing the probe assembly to pass therethrough and guiding the probe assembly into the through-hole, and an outer wall, whereby the probe assembly is guided into the through-hole through the guide slit, and the ultrasonic probe is inserted into the through-hole to be attached to the adapter; and
 a finger grip portion extending from the outer wall of the body and allowing the operator's fingers to be hooked thereon.

Accordingly, the cable is guided into the through-hole through the guide slit, and the ultrasonic probe is inserted in the through-hole and attached to the adapter. When the probe is pulled out from the through-hole of the body, the cable is located in the through-hole. Since the cable is taken out from the through-hole through the guide slit, the adapter can be quickly and easily detached from the cable.

Therefore, operability for attaching/detaching the adapter to/from the probe is improved.

In addition, according to the present invention, there are provided a first engaging portion formed in the probe, and a second engaging portion formed on the body of the adapter and engaged with the first engaging portion. The adapter is set at a predetermined position of the probe by engaging the first engaging portion of the probe with the second engaging portion of the adapter. Therefore, the adapter can be quickly and easily attached to an arbitrary position of the probe.

Furthermore, according to the present invention, a positioning means for positioning the adapter to a predetermined position of the probe comprises a flexible member having flexibility and a pair of edges defining the guide slit, and defining the through-hole of the body. Therefore, when the second engaging portion of the adapter is engaged with the first engaging portion of the probe, the flexible member is urged against the probe, and the second engaging portion is clicked and engaged with the first engaging portion. Thus, the adapter can be quickly and easily attached to an arbitrary position of the probe. Furthermore, the adapter can be stably attached to the probe. More specifically, when fingers are hooked on the finger grip portion, the adapter is not accidentally moved in an extending direction of the probe or is not rotated around the probe. Moreover, the adapter according to the present invention has a very simple structure.

BRIEF DESCRIPTION OF THE DRAWINGS

FIG. 5 is a perspective view of the probe and the adapter in FIG. 3, showing a state wherein the adapter is attached to the probe;

FIG. 6 is a side view of the adapter in FIG. 3;

FIG. 7 is a sectional view taken along the line VII—VII in FIG. 6;

DETAILED DESCRIPTION OF THE PREFERRED EMBODIMENT

FIGS. 3 to 10 show pencil type ultrasonic probe 21, according to the present invention, to which adapter 50 is attached.

First, pencil type ultrasonic probe 21 will be described. This pencil type ultrasonic probe has a diagnosis area smaller than that of a normal ultrasonic probe. For this reason, the pencil type ultrasonic probe is used to diagnose a newborn baby and a child whose body size is small. For example, a beam radiation surface of this probe is located on a suprasternal portion of a child to observe the motion of the valves of the heart. Then, the flow speed of the blood flowing through the heart is measured and a tomographic image of the heart is obtained.

Figure 3:
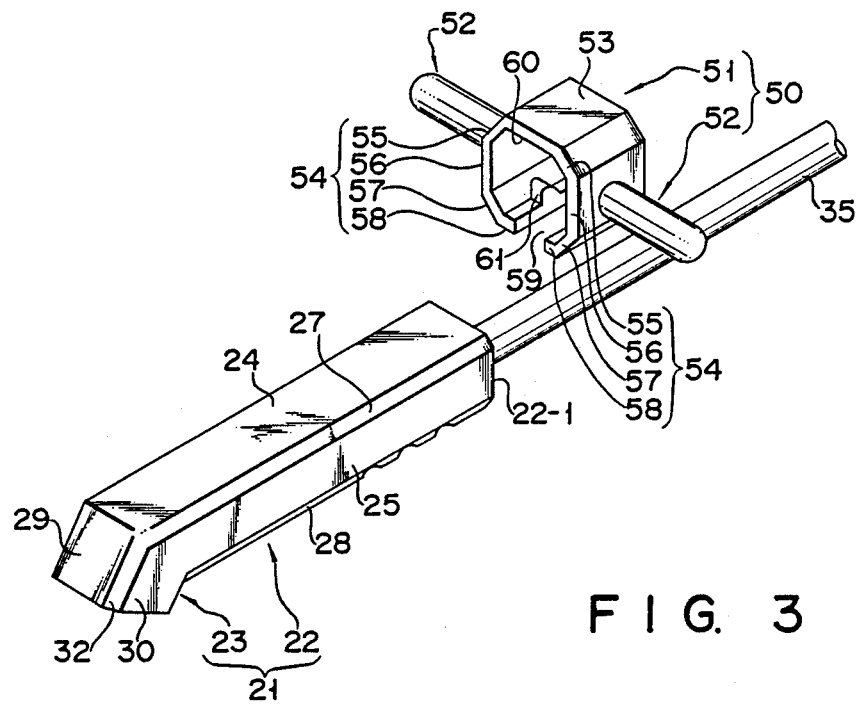
FIG. 3 is a perspective view of a pencil type ultrasonic probe provided with a finger grip adapter, according to the present invention.
Figure 4:
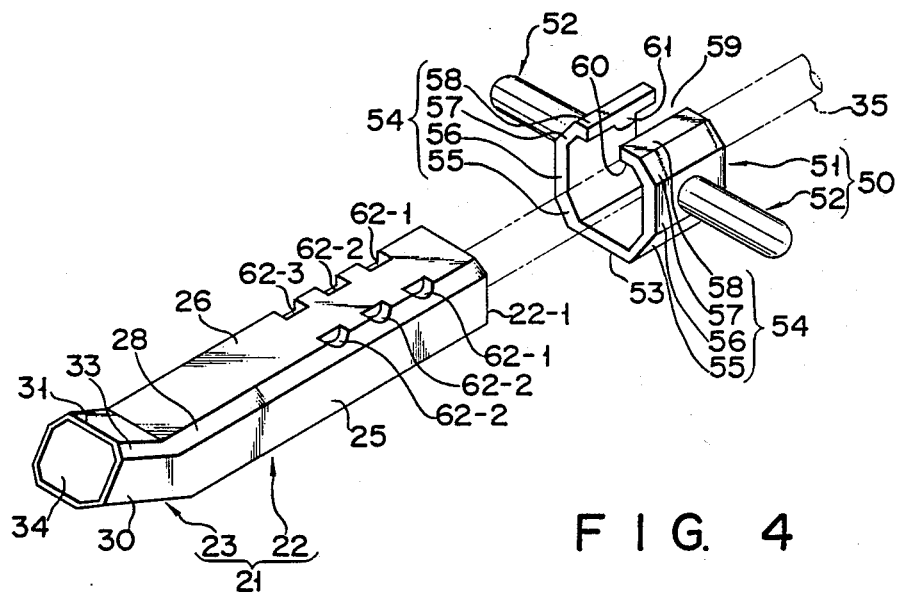
FIG. 4 is a perspective view of the probe and the adapter in FIG. 3 when observed from the bottom.

As shown in FIGS. 3 and 4, pencil type ultrasonic probe 21 comprises extended portion 22 extended by a predetermined length and distal end portion 23 bent at a predetermined angle with respect to extended portion 22. Extended portion 22 has a non-circular cross section. More specifically, extended portion 22 includes upper wall 24, a pair of side walls 25, and lower wall 26. The width of upper wall 24 is substantially equal to that of lower wall 26. First and second chamfered portions 27 and 28 are, respectively, formed between upper and side walls 24 and 25, and lower and side walls 26 and 25. The cross-sectional shape of extended portion 22 is substantially uniform. Similarly, distal end portion 23 includes upper wall 29, a pair of side walls 30, lower wall 31, and chamfered portions 31 and 32. In distal end portion 23, beam radiation surface 34 for emitting an ultrasonic beam is defined.

Cable 35 for transmitting an electrical signal is connected to the proximal end 22-1 of extended portion 22. The outer diameter of cable 35 is set to be smaller than the distance between upper and lower walls 24 and 26 of the extended portion, and to be smaller than the distance between side walls 25. Cable 35 is connected to an ultrasonic diagnosis apparatus (not shown). A probe assembly is defined by cable 35 and pencil type ultrasonic probe 21.

Figure 10:
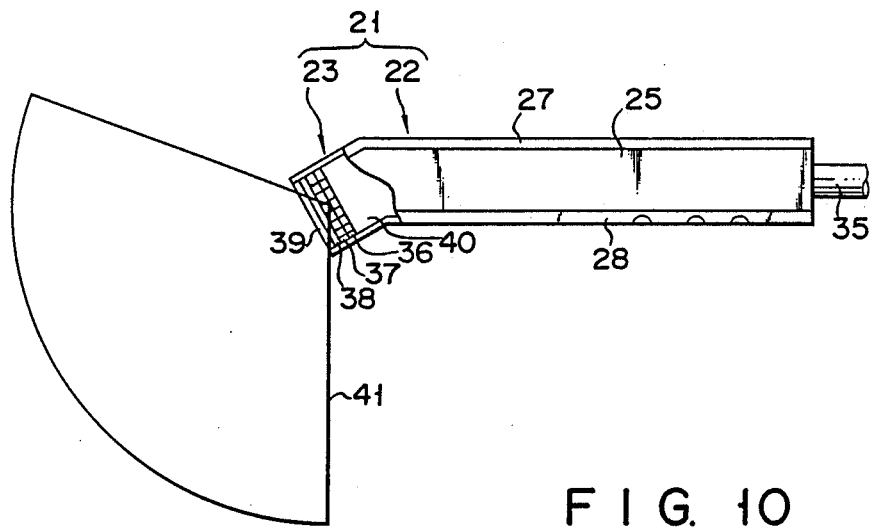
FIG. 10 is a front view of the probe in FIG. 3 (including a partially cutaway section view)

As shown in FIG. 10, distal end portion 23 comprises a plurality of transducer elements 36 arrayed in a row. Transducer elements 36 are connected to the ultrasonic diagnosis apparatus through cable 35. A plurality of matching layers 38 are, respectively, arranged to abut against transducer elements 36. Another matching layer 38 is arranged to abut against matching layers 37. Acoustic lens 39 is arranged to abut against matching layer 38. In addition, backing member 40 for absorbing unnecessary ultrasonic waves is arranged to abut against transducer elements 36.

In a pencil type ultrasonic probe having a plurality of transducer elements, an ultrasonic diagnosis is performed in mainly the B mode, M mode, and the Doppler mode. In the B mode for obtaining a tomographic image inside a patient to be examined, mainly sector scanning and linear scanning are performed. In the sector scanning, a predetermined electrical signal is supplied from the ultrasonic diagnosis apparatus to each transducer element 36 through cable 35 at predetermined time intervals. As a result, transducer elements 36 sequentially emit ultrasonic waves toward acoustic lens 39 at predetermined time intervals. These ultrasonic waves are synthesized to define an ultrasonic beam. This ultrasonic beam is deflected. Then, as shown in FIG. 10, an inner portion of the patient is scanned in a sector-like manner (i.e., the ultrasonic beam scans inside the patient along scanning surface 41 in FIG. 10). The ultrasonic beam (echo) reflected inside the patient is detected by transducer elements 36, and then tomographic image inside the patient is displayed on a cathode-ray tube (not shown). In the linear scanning, electrical signals are supplied to a predetermined number of transducer elements 36 at predetermined time intervals. Transducer elements 36 generate ultrasonic waves. Each ultrasonic wave linearly scans inside the patient. As a result, a tomographic image is displayed on the cathode-ray tube.

A plurality of transducer elements are arrayed in a line between upper and lower walls 29 and 31. With this arrangement, in the B mode, scanning surface 41 is defined to be parallel to side wall 30.

In the Doppler mode, when ultrasonic waves are generated from the transducer elements, these ultrasonic waves are reflected by, e.g., the flowing blood, and then detected by the transducer elements. In this case, the frequency of the reflected ultrasonic waves is different from that of the emitted ultrasonic waves due to the Doppler effect. The difference between the two frequencies is proportional to a vector component of the flow speed of the blood. As a result, the difference between the frequencies is calculated to measure the flow speed of the blood, and then the resultant value is displayed on, e.g., the cathode-ray tube. In the Doppler mode, either pulsed ultrasonic waves or continuous ultrasonic waves are used.

In the M mode, pulsed ultrasonic waves are generated from the transducer elements, reflected by a moving portion (e.g., a valve of the heart), and then detected by the transducer elements. The relationship between the elapsed time and the position of the moving portion is obtained. As a result, changes in moving portion are displaced as a function of time on the cathode-ray tube.

A pencil type ultrasonic probe of a single type comprises only one transducer element. According to this type, only one pulsed ultrasonic wave is emitted, and reflected to be detected. In this pencil type ultrasonic probe, mainly, changes in moving portion are observed as a function of time in the M mode, and the flow speed of the blood flowing through the heart and veins is measured in the Doppler mode.

The beam radiation surfaces of these probes must be stably held with respect to the patient. Especially, when the probe having a plurality of transducer elements is to be used, since a tomographic image is obtained, the probe must be held more stably than the probe of the single type.

Finger grip adapter 50 to be attached to a pencil type ultrasonic probe according to the present invention will now be described.

Adapter 50 comprises body 51 in which extended portion 22 of probe 21 is inserted, and a pair of finger grip portions 52 protruding from an outer wall surface of body 51.

The inner surface of body 51 is formed into a shape corresponding to the outer shape of extended portion 22 when extended portion 22 is inserted in body 51. More specifically, the inner surface of body 51 is formed into a non-circular shape so as to correspond to the outer shape of extended portion 22. Body 51 comprises base 53 having an inner surface corresponding to upper wall 24 of extended portion 22, and a pair of arm portions 54 extending from base 53 in its both side directions. Each arm portion 54 comprises first inclined portion 55 having an inner surface corresponding to first chamfered portions 27, side portion 56 having an inner surface corresponding to outer side walls 25, second inclined portion 57 having an inner surface corresponding to second chamfered portions 28, and lower portion 58 having an inner surface corresponding to part of lower wall 26. In other words, through-hole 60 corresponding to the outer shape of extended portion 22 is defined by the inner space between base 53 and arm portions 54.

Guide slit 59 for guiding cable 35 into through-hole 60 is defined by a pair of distal end portions of arm portions 54, i.e., a pair of edges of lower portions 58. The gap in guide slit 59, i.e., the distance between the pair of lower portions 58, is set to be slightly larger than the diameter of cable, and smaller than the distance between outer side walls 25 of extended portion 22. Guide slit 59 causes through hole 60 to communicate with an external portion.

Base 53 and arm portions 54 constituting body 51 are integrally formed using a resin having flexibility. That is, body 51 is defined by a flexible or elastically deformable member. As indicated by imaginary lines in FIG. 6, distance v between lower portions of side portions 56 of arm portions 54 is set to be smaller than distance u between upper portions thereof. In other words, the gap in guide slit 59 when the adapter is not attached to the probe is smaller than that when the adapter is attached to the probe. For this reason, when the adapter is attached to the probe, arm portions 54 are moved so as to widen the gap in guide slit 59. Therefore, upon attachment of the adapter, arm portions 54 are urged against the outer surface of extended portion 22 of the probe.

A pair of engaging projections 61 are formed on the inner upper surface of the pair of lower portions 58. A plurality of pairs of recesses 62-1, 62-2, and 62-3 are formed in lower wall 31 of extended portion 22 to be engaged with projections 61. The plurality of pairs 62-1, 62-2, and 62-3 are arranged in this order in the extending direction of extended portion 22.

As shown in FIGS. 4 and 7, each engaging projection 61 has a semicircular cross section, and each of recesses 62-1, 62-2, and 62-3 also has a semicircular cross section. When the engaging projections are engaged with the recesses, lower portions 58 of arm portions 54 are urged against the outer surface of extended portion 22. For this reason, the engaging projections are clicked and engaged with the recesses. That is, the probe provided with the adapter, according to the present invention, comprises a click engaging mechanism.

When engaging projections 61 are engaged with recesses 62-1, 62-2, and 62-3, body 51 is positioned to a predetermined position of extended portion 22. More specifically, the adapter can be attached to an arbitrary position of the extended portion of the probe by selecting the recesses with which the engaging projections are engaged.

Finger grip portion 52 extends from side portion 56 of arm portion 54. The cross section of finger grip portion 52 is formed into a circular shape. Finger grip portion 52 extends by a length allowing at least one finger to be hooked thereon.

A process will be described, wherein adapter 50 according to the present invention is attached to pencil type ultrasonic probe 21.

As shown in FIGS. 4 and 5, the longitudinal direction of guide slit 59 of the adapter and the extending direction of cable 35 coincide with each other. Cable 35 is guided through guide slit 59 into the inner space between base 53 and arm portions 54, i.e., through-hole 60. Body 51 of the adapter is moved to proximal end 22-1 of the probe while cable 35 is located in through-hole 60.

Arm portions 54 are moved so as to slightly widen the gap in guide slit 59, and the diameter of through-hole 60 is made slightly larger, thereby allowing proximal end 22-1 of extended portion 22 to pass through through-hole 60. Subsequently, body 51 of the adapter is moved in an axial direction of extended portion 22. At this time, since arm portions 54 are urged against the outer surface of extended portion 22, resistance to the sliding movement is generated between the inner surfaces of arm portions 54 and the outer surface of extended portion 22. When body 51 is moved in the axial direction of extended portion 22 by a predetermined distance against this resistance, engaging portions 61 formed on lower portions 58 of arm portions 58 are brought into contact with proximal end 22-1 of extended portion 22. Since engaging projections 61 have semicircular cross sections, they are slid over lower wall 26 of extended portion 22. In addition, since engaging projections 61 are located between lower wall 26 of extended portion 22 and lower portions 58 of arm portions 54, part of arm portions 54 is deformed and separated from the outer surface of extended portion 22. As a result, the resistance to the sliding movement is decreased.

When body 51 is moved in the axial direction of extended portion 22 by a predetermined distance, engaging projections 61 are clicked and engaged with either of recesses 62-1 to 62-3 formed in lower wall 26 of extended portion 22. In this case, since the pressing force of arm portions 54 is applied to the outer surface of extended portion 22, engaging projections 61 cannot be easily detached from recesses 62-1 to 62-3. Accordingly, when the projections are engaged with the recesses, the adapter is positioned to the predetermined position of the extended portion of the probe while body 51 of the adapter cannot be easily moved in the axial direction of extended portion 22.

Adapter 50 is detached from pencil type ultrasonic probe 21 in the following manner. Arm portions 54 are moved so as to widen the gap in guide slit 59 against the pressing force of arm portions 54, thereby releasing the engagement between engaging projections 61 and recesses 62-1 to 62-3. For example, body 51 is forcibly moved in the axial direction of extended portion 22 with predetermined strength more than the pressing force of arm portions 54. Accordingly, arm portions 54 are moved so as to widen the gap in guide slit 59. As a result, the engagement between engaging projections 61 and recesses 62-1 to 62-3 is released. Body 51 is moved toward proximal end 22-1 of extended portion 22. When proximal end 22-1 of extended portion 22 is pulled out from through-hole 60 of body 51, cable 35 is located in through-hole 60 of body 51. Cable 35 is taken out from through-hole 60 through guide slit 59. With this operation, the adapter is completely detached from the ultrasonic probe.

A method of using this adapter and an operation of the pencil type ultrasonic probe will be described with reference to FIGS. 8 and 9.

Figure 8:
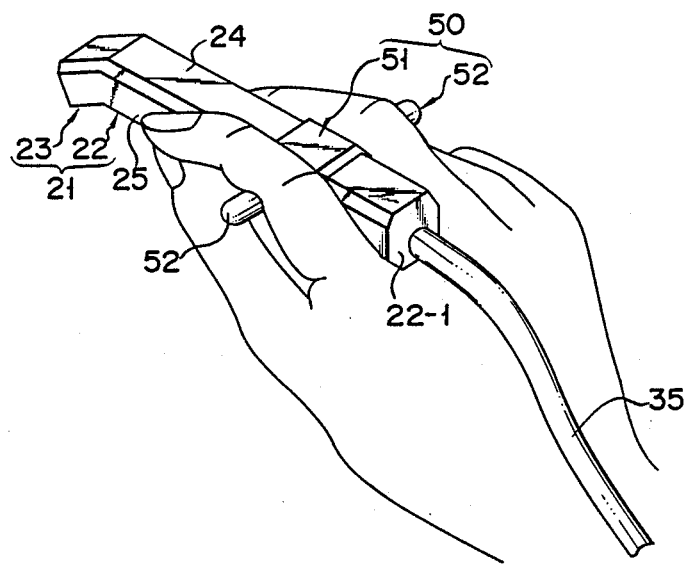
FIG. 8 is a perspective view showing a state wherein the probe is operated with the adapter attached thereto.

FIG. 8 shows a case wherein the probe is operated with the adapter, according to the present invention, attached thereto. FIG. 9 shows a case wherein the probe is operated without attaching the adapter thereto.

When the adapter is attached to the probe, the probe is located between the index and middle fingers. proximal end 22-1 of extended portion 22 of the probe is positioned on the web of the hand located between the roots of the index and middle fingers. The index and middle fingers are respectively hooked on the pair of finger grip portions 52 of the adapter. The thumb is urged against side or lower wall 25 or 26 of extended portion 22. Cable 35 extends over the back of the hand. By using the adapter n this manner, the probe is held by the operator's hand with a relatively large number of support points. For this reason, the probe is stably held by the operator's hand. As a result, beam radiation surface 34 of the probe is stably maintained with respect to the patient without being accidentally moved.

Figure 9:
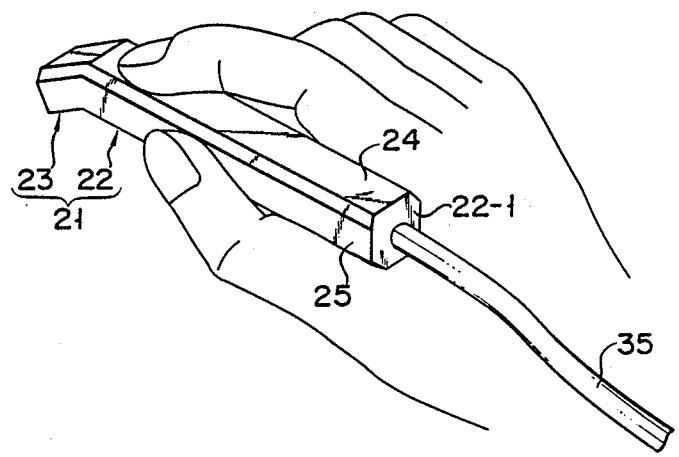
FIG. 9 is a perspective view showing a state wherein the probe is operated without attaching the adapter thereto.

As shown in FIG. 9, when the adapter is not attached to the probe, the probe is positioned between the thumb and the index finger. Proximal end 22-1 of extended portion 22 of the probe is positioned in the web of the hand located between the roots of the thumb and index finger. The thumb is urged against one of side walls 25, the index finger is urged against upper wall 24 of the extended portion, and the middle finger is urged against the other of side walls 25. Cable 35 extends over the back of the hand. Accordingly, even when the adapter is not attached to the probe, the probe can be relatively stably held by the operator's hand.

Figure 1:
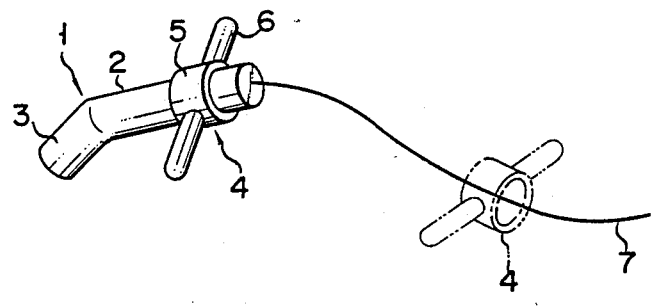
FIGS. 1 and 2 are perspective views respectively showing conventional pencil type ultrasonic probes and finger grip adapters to be attached thereto.
Figure 2:
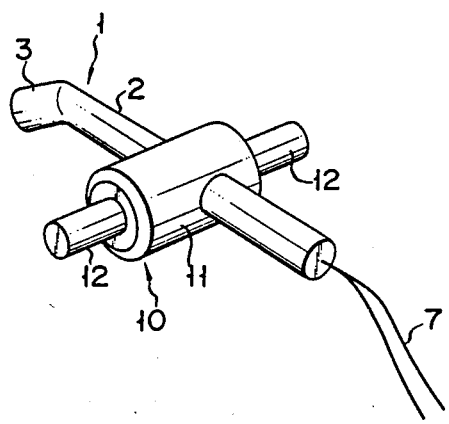

According to the present invention, body 51 comprises through-hole 60, through which extended portion 22 of the probe can pass, and guide slit 59 for guiding cable 35 into through-hole 60. More specifically, cable 35 is guided into through-hole 60 through guide slit 59, and then the extended portion is inserted into through-hole 60, thereby attaching the adapter to the probe. In addition, after extended portion 22 is pulled out from through-hole 60, cable 35 is taken out from through-hole 60 through guide slit 59. Therefore, the adapter can be completely, quickly, and easily attached/detached to/from the probe assembly defined by the probe and the cable. As shown in FIGS. 1 and 2, in the conventional adapters, when the pencil type ultrasonic probe is pulled out from the through-hole of the adapter, the cable is still inserted in the through-hole of the adapter. For this reason, when the conventional probe is operated without attaching the adapter thereto, the adapter may hit the operator's arm or hand. As a result, the adapter may interfere with the operator who is operating the probe during an ultrasonic diagnosis. In contrast to this, according to the present invention, the adapter can be completely attached/detached to/from the probe. Therefore, when the probe is operated without attaching the adapter thereto, the adapter does not hit the operator's hand or arm, and the operator's probe operation is not interfered.

The pencil type ultrasonic probe is formed into a non-circular shape and the inner surface (i.e., the through hole) of the adapter is formed into an non-circular shape so as to correspond the outer shape of extended portion 22 of the probe. For this reason, the adapter is not rotated about the axial line of extended portion 22. Therefore, the adapter can be stably attached to the probe.

Each of base 53 and arm portions 54 constituting body 51 of the adapter is made of a resin having flexibility. In addition, the gap of the guide slit when the adapter is not attached to the probe is set to be slightly smaller than that of the guide slit when the adapter is not attached to the probe. For this reason, the diameter of through-hole 60 when the adapter is not attached to the probe is smaller than that of through hole 60 when the adapter is attached to the probe. When the adapter is attached, arm portions 54 are moved with respect to base 53 so as to widen the gap of guide slit 59. Consequently, arm portions 54 are urged against the outer surface of extended portion 22. This arrangement further prevents body 51 from being rotated about the axial line of extended portion 22. The adapter is much stably attached to the probe. Therefore, when the fingers are hooked on finger grip portions 52, the adapter is not accidentally rotated about the axial line of extended portion 22 during an ultrasonic diagnosis.

In addition, arm portions 54 are urged against the outer surface of extended portion 22. For this reason, when body 51 is moved in the axial direction of extended portion 22, resistance to the sliding movement is generated between the inner surface of arm portions 54 and the outer surface of extended portion 22. Therefore, even if the click engaging mechanism according to the present invention is not arranged on the adapter, the adapter can be stopped at an arbitrary position of extended portion 22, and the adapter is not accidentally moved in the axial direction of extended portion 22.

In addition, the probe and the adapter comprise the click engaging mechanism. More specifically, when body 51 of the adapter is moved in the axial direction of extended portion 22 and engaging projections 61 are positioned to recesses 62-1 to 62-3, engaging projections 61 are clicked and engaged with recesses 62-1 to 62-3 by the pressing force of arm portions 54. In order to release this engagement, arm portions 54 are moved against the pressing force thereof so as to widen the gap in guide slit 59. For example, body 51 is forcibly moved in the axial direction of extended portion 22 with predetermined strength more than the pressing force of arm portions 54. Then, arm portions 54 are moved so as to widen the gap in guide slit 59. As a result, the engagement between engaging projections 61 and recesses 62-1 to 62-3 is released.

Accordingly, when engaging projections 61 are engaged with either of recesses 62-1 to 62-3, body 51 can be positioned at a predetermined position of extended portion 22. Thus, the adapter can be attached to an arbitrary position of the extended portion by changing the setting positions of the recesses. In addition, since the pressing force of arm portions 54 is applied to the outer surface of extended portion 22, engaging projections 61 are engaged with the recesses while being urged against the recesses. In order to move the adapter in the axial direction of the extended portion, a large force is required. When the fingers are hooked on finger grip portions 52 during an ultrasonic diagnosis, the adapter is not accidentally moved in the axial direction of the extended portion. The adapter shown in FIG. 2 can be stopped at an arbitrary position of the extended portion. However, in this conventional adapter, the thread is accidentally loosened. For this reason, the conventional adapter may be accidentally moved in the axial direction of the extended portion during an ultrasonic diagnosis.

Furthermore, by moving the arm portions so as to widen the gap in the guide slit, engaging projections 61 are easily and quickly moved to one pair of recesses to another pair of recesses. That is, the adapter according to the present invention can be extremely easily and quickly set to a predetermined position of the extended portion of the adapter. The adapter shown in FIG. 2 is set to a predetermined position by fastening the thread upon loosening thereof. Therefore, the process of setting the adapter to the predetermined position of the probe is cumbersome and requires a relatively long period of time.

As has been described above, according to the present invention, the adapter can be completely, quickly, and easily detached from the probe and cable. The adapter can be quickly and easily attached to an arbitrary position of the extended portion of the probe. Therefore, the adapter has excellent operability of being attached/detached to/from the probe. In addition, the adapter can be stably attached to the probe. More specifically, when the fingers are hooked on the finger grip portions, the adapter is not accidentally moved in the extending direction of the extended portion or is not rotated about the extended portion. Moreover, the adapter has a very simple structure.

Figure 11:
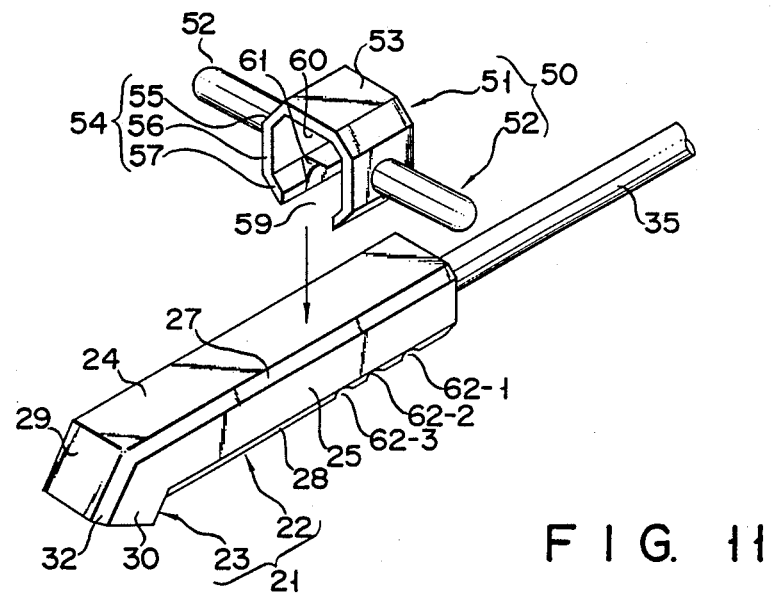
FIG. 11 is a perspective view showing a modification of a pencil type ultrasonic probe provided with a finger grip adapter, according to the present invention.

FIG. 11 shows a modification of the adapter.

According to this modification, when an adapter is not attached to a probe, the gap in guide slit 59 of arm portions 54 is increased compared with that in the above-described embodiment. More specifically, lower portions 58 are not formed on arm portions 54. With this arrangement, extended portion 22 can be directly passed through guide slit 59 and guided into through-hole 60, instead of guiding the cable into through-hole 60 through guide slit 59.

When the adapter is attached to the probe, the guide slit is positioned to upper wall 24 of extended portion 22, and the distal end portions of arm portions 54 are urged against extended portion 22. As a result, arm portions 54 cover extended portion 22 while the gap in the guide slit is widened by a degree corresponding to the distance between the pair of side walls 25 of extended portion 22 against the pressure of arm portions 54. When extended portion 22 is inserted into through-hole 60 of body 51, the gap in guide slit 59 is narrowed due the pressing force of arm portions 54, and hence arm portions 54 are urged against extended portion 22. Subsequently, body 51 is moved in the axial direction of extended portion 22, and engaging projections 61 are clicked and engaged with recesses 62-1 to 62-3, thereby positioning body 51 to a predetermined position of extended portion 22.

When the adapter is to be detached from the probe, arm portions 54 are moved against the pressing force thereof so as to widen the gap in guide slit 59 to be larger than the distance between the side walls of extended portion 22. Under this condition, extended portion 22 is pulled out from through-hole 60 of body 51 through guide slit 59. As a result, the adapter can be completely detached from the probe.

As has been described above, according to the modification, the adapter is attached/detached to/from the probe by directing passing the extended portion through the guide slit. Therefore, attachment/detachment of the adapter to/from the probe can be further quickly and easily performed compared with the above-described embodiment.

What is claimed is:

1. A probe assembly and a finger hook adapter attached thereto,
    said probe assembly comprising:
    a pencil-type ultrasonic probe including an elongated body and a transducer element arranged at a distal end of the elongated body; and
    a cable including one end fixed to a proximal end of the elongated body and another end adapted to be connected to an ultrasonic diagnosis apparatus,
    said finger hook adapter comprising:
    an elastically deformable member having inner surfaces defining a shape similar to an outer shape of said elongated body, said inner surfaces forming a through-hole in which the elongated member of said probe is adapted to be inserted, said member formed with a guide slit for guiding the cable into the through-hole, and an outer wall, said deformable member being elastically deformed when the cable is pressed against the guide slit, in a manner to widen a gap of the guide slit, and being elastically deformed when the proximal end of the elongated body is pressed against the inner surfaces forming the through-hole, in a manner to slightly widen the through-hole and to allow the elongated body to be inserted into the through-hole, whereby the elastically deformable member is elastically held by the elongated body; and
    a rod-shaped finger hook member extending from the outer wall of the ring-shaped member, said rod-shaped finger hook member adapted for allowing fingers of an operator to be hooked thereon, to keep said probe at a predetermined position with respect to the operator.

2. A probe according to claim 1, wherein said guide slit has a gap for allowing said cable to pass therethrough and guiding said cable into said through-hole.

3. A probe according to claim 2, further comprising an extended portion extending from said distal end of said elongated body by a predetermined length, to which said cable is fixed, and a distal end portion coupled to said extended portion and storing said transducer element, and said through-hole has a diameter allowing said extended portion of said ultrasonic probe to be inserted therethrough to cause said body to be attached to said extended portion, whereby said cable is guided into said through-hole through said guide slit, and said extended portion of said ultrasonic probe is inserted into said through-hole through said body of said adapter to be attached to said ultrasonic probe.

4. A probe according to claim 3, wherein said elongated body comprises rotation preventing means for preventing said body of said adapter from being rotated around said extended portion of said probe.

5. A probe according to claim 4, wherein said rotation preventing means includes means for forming a cross-sectional shape of said extended portion of said probe into any other shape than circular shape, and means for forming a cross-sectional shape of said through-hole of said body into any other shape than circular shape so as to correspond to the cross-sectional shape of said extended portion.

6. A probe according to claim 3, further comprising movement preventing means for preventing said body of said adapter from being moved in an extending direction of said extended portion of said probe.

7. A probe according to claim 3, further comprising positioning means for positioning said body of said adapter to a predetermined position of said extended portion of said probe.

8. A probe according to claim 7, wherein said positioning means includes a first engaging portion formed in said extended portion of said probe and a second engaging portion formed on said body of said adapter and engaged with said first engaging portion when said extended portion is inserted into said through-hole.

9. A probe according to claim 8, wherein said first engaging portion is a recess, and said second engaging portion is an engaging projection to be engaged with said recess.

* * * * *